(12) United States Patent
Xing et al.

(10) Patent No.: US 11,214,530 B2
(45) Date of Patent: Jan. 4, 2022

(54) METHOD FOR THE SEPARATION OF C4 OLEFIN MIXTURES

(71) Applicant: ZHEJIANG UNIVERSITY, Hangzhou (CN)

(72) Inventors: Huabin Xing, Hangzhou (CN); Zhaoqiang Zhang, Hangzhou (CN); Qiwei Yang, Hangzhou (CN); Qilong Ren, Hangzhou (CN); Zongbi Bao, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 16/618,982

(22) PCT Filed: Nov. 27, 2017

(86) PCT No.: PCT/CN2017/113005
§ 371 (c)(1),
(2) Date: Dec. 3, 2019

(87) PCT Pub. No.: WO2019/037317
PCT Pub. Date: Feb. 28, 2019

(65) Prior Publication Data
US 2020/0172454 A1 Jun. 4, 2020

(30) Foreign Application Priority Data
Aug. 22, 2017 (CN) .......................... 201710724645.3

(51) Int. Cl.
*C07C 7/11* (2006.01)
*B01D 53/04* (2006.01)
(Continued)

(52) U.S. Cl.
CPC ................ *C07C 7/11* (2013.01); *B01D 53/04* (2013.01); *B01J 20/226* (2013.01); *B01J 20/282* (2013.01);
(Continued)

(58) Field of Classification Search
None
See application file for complete search history.

(56) References Cited

U.S. PATENT DOCUMENTS

| 2014/0060326 A1* | 3/2014 | Sundaram | B01D 53/06 95/96 |
| 2015/0291641 A1* | 10/2015 | Zaworotko | B01D 53/02 95/139 |
| 2015/0329563 A1* | 11/2015 | Kishida | C07F 1/08 95/50 |

FOREIGN PATENT DOCUMENTS

| CN | 105163846 | 12/2015 |
| CN | 105944680 | 9/2016 |

(Continued)

OTHER PUBLICATIONS

Mastropietro et al. "Guanine-containing copper(II) complexes: synthesis, X-ray structures and magnetic properties" Dalton Transactions 2008, 514-520. (Year: 2008).*

(Continued)

*Primary Examiner* — Philip Y Louie
*Assistant Examiner* — Alyssa L Cepluch
(74) *Attorney, Agent, or Firm* — Jiwen Chen; Jacobson Holman PLLC (57) ABSTRACT

A method for the separation of C4 olefin mixtures using anion-pillared hybrid porous materials as physical adsorbents is provided. The anion-pillared hybrid porous material was constructed by metal ions (M), organic ligand (L), and inorganic anion (A), forming a three-dimensional structure (A-L-M). C4 olefin mixtures contact with hybrid porous (Continued)

materials in certain ways, then each single C4 olefin monomer can be obtained. The pore size of anion-pillared hybrid porous materials and the spatial configurations of the anions within the pores can be fine-tuned and pre-designed. C4 olefins with different size and shape can be efficiently separated by the anion-pillared hybrid porous materials through shape recognition and size-sieving mechanism.

4 Claims, 7 Drawing Sheets

(51) Int. Cl.
    *B01J 20/22*    (2006.01)
    *B01J 20/282*    (2006.01)

(52) U.S. Cl.
    CPC .... *B01D 2253/204* (2013.01); *B01D 2256/24* (2013.01); *B01D 2257/7022* (2013.01); *B01D 2259/40083* (2013.01); *B01D 2259/40086* (2013.01); *B01J 2220/56* (2013.01); *B01J 2220/58* (2013.01)

(56) References Cited

FOREIGN PATENT DOCUMENTS

CN         106478337         3/2017
JP         2014088341 A  *  5/2014
WO     WO-2016162834 A1  *  10/2016  .......... B01J 31/1691

OTHER PUBLICATIONS

Pham et al. "Theoretical Investigations of CO2 and H2 Sorption in an Interprenetrated Square-Pillared Metal-Organic Material" Journal of Physical Chemistry C 2013, 117, 9970-9982. (Year: 2013).*

Machine translation JP 2014-088341, original published May 15, 2014, translation accessed May 3, 2021 (Year: 2021).*

Yang et al. "Unusual Polymeric ZnII/CdII Complexes with 2,6-Diaminopurine by Synergistic Coordination of Nucleobases and Polycarboxylate Anions: Binding Behavior, Self-Assembled Pattern of the Nucleobase, and Luminscent Properties" Crystal Growth & Design 2009, vol. 9, 4933-4944. (Year: 2009).*

* cited by examiner

METHOD FOR THE SEPARATION OF C4 OLEFIN MIXTURES

This is a U.S. national stage application of PCT Application No. PCT/CN2017/113005 under 35 U.S.C. 371, filed Nov. 27, 2017 in Chinese, claiming priority of Chinese Application No. 201710724645.3, filed Aug. 22, 2017, all of which is hereby incorporated by reference.

INTRODUCTION

The present invention relates to a chemical engineering field, and in particular to a method of adsorptive separation of C4 olefin mixtures using anion-pillared hybrid porous materials.

BACKGROUND

C4 olefins mainly including 1,3-butadiene, 1-butene, 2-butene and isobutene, are mainly produced from the C4 fraction of cracking gases of petroleum, and small amounts come from natural gas and recovered gas from oil. C4 olefins exhibit high values in chemical industry, and are basic organic raw materials for the production of a variety of synthetic rubbers and chemicals. Each high-purity C4 olefin has important application value in the chemical industry. They are mainly used as polymerized monomers to produce polybutene resins and butyl rubbers, alkylating agents, and to produce butanol/ketone/aldehyde and oil blending components. For example, 1,3-butadiene is mainly used for the synthesis of styrene-butadiene, polybutadiene rubbers and styrene-butadiene latex; 1-butene can be used for the production of 1,2-butanediol, secondary butanol, bio-cyclozole, pesticides, butadiene, butanol, maleic anhydride, acetic acid, and low-density linear polyethylene and other downstream products. Iso-butene is an important raw material for fine chemical industry. High purity iso-butene (>99%) is widely used as monomers or intermediate for methyl acrylonitrile, butyl rubber and polyisobutene production. 90% pure isobutylene can be used to produce methacrylic acid, isoprene, etc.

Currently, industrial separation of 1,3-butadiene, 1-butene, and iso-butene is performed mainly by solvents absorption, extractive distillations, cryogenic distillations, and adsorption by zeolites. Solvent absorption is the main method for 1, 3-butadiene purification. For example, CN Patents 102992933A and 101160275A, U.S. Pat. Nos. 9,266, 795B2, 6,040,489 and 4,128,457 disclosed the using of acetonitrile, dimethyl formamide and methylpyrrolidone solvents for absorption or extractive distillation to produce 1, 3-butadiene of high purity. However, this method has the disadvantages of serious loss of solvents and high energy consumption. Chemical reaction and reaction distillation are common methods used for the removal of iso-butenes from C4 olefins. At present, the industry mainly uses the MTBE method and the hydrated t-butanol method. In MTBE method, iso-butene reacts with methanol forming MTBE, the conversion efficiency of iso-butene can reach 99.55%, but only after decomposition of MTBE, iso-butene can be obtained. In addition, Chinese patent 101492334A disclosed a method to isomerize iso-butenes to 2-butenes, and then can separate iso-butenes from 2-butenes due to the different boiling points. This method exhibits the disadvantage of high energy input, also produces a large amount of liquid chemicals. Precise distillation is the main technology used for 1-butene refining. High purity 1-butene can be obtained from etherified C4 mixtures, but the relative volatility of 1-butene and n-butane is only 1.10, which results in more than 140 theoretical trays needed. Japanese Zeon Corporation also provided the method to separate 1-butenes from etherified C4 mixtures, but more than 200 trays are required in the separation columns.

Recently, CN102329180A and CN102329183A utilize 5A molecular sieves to adsorb by using multi-stage bed, desorbing n-hexane in the adsorption tower and adsorbing 1-butene, and simultaneously producing 1-butene and isobutylene. CN104030874A adopts three-column or multi-column pressure swing adsorption, and the adsorbent is carbon molecular sieve to obtain isobutylene. CN102329179A adopts modified 5A molecular sieve to adsorb gas phase C4 material. CN102351630A uses a lanthanum or potassium modified X or Y zeolite molecular sieve to adsorb a liquid phase C4 material. In addition, although the molecular sieve can be reported to achieve partial C4 component separation, the molecular sieve adsorbent has a small adsorption capacity for the C4 fraction and low separation selectivity.

In recent years, metal-organic frameworks (MOFs) as new emerging porous materials have been found to exhibit separation potential for C4 mixtures. Banglin Chen et al. reported that ZJNU-30 constructed by $Zr^{4+}$ and 1,3,5-trisubstituted phenyl-4,4,4-naphthene benzoic acid exhibited high capacity for C4 hydrocarbons, but the selectivity was very low (1.15) (A porous zirconium-based Metal-organic framework with the potential for the separation of butene isomers, *Chemistry—A European Journal*, 2016, 22, 14988-14997). Prof. Susumu Kitagawa in Kyoto University reported a flexible material, SD-65, can selectively capture 1,3-butadiene, however, the capacity was low (1.8 mmol/g) (Recognition of 1,3-butadiene by a porous coordination polymer, Angew. Chem. Int. Ed., 2016, 55, 13784-13788), and SD-65 exhibited almost no separation selectivity for C4 mixtures due to flexibility of the frameworks. It is imperative to develop efficient materials for separation. However, the trade-off effect between capacity and selectivity exerts great barriers for such task to design and develop energy-efficient materials for C4 separation.

SUMMARY OF THE INVENTION

The present invention provides a method to separate C4 olefin mixtures using anion-pillared hybrid porous materials as adsorbents to achieve highly effective separation.

The anion-pillared hybrid porous materials in the present invention are constructed by metal-ions, inorganic anions, and organic ligands. This kind of crystal material exhibits high surface area, high pore volumes, and abundant inorganic anions lined by the pore walls. The pore size, shape, and the deposited position of the functional sites can be finely tuned by altering the kinds of inorganic anions, organic likers and metal ions. The kinetic diameters of 1,3-butadiene, 1-butene, cis-2-butene, trans-2-butene, and isobutene is 4.24, 4.83, 4.49, 4.62, 4.84 Å, respectively. Expect for the difference in molecular size of each C4 olefin, the spatial configurations of hydrogen atoms on olefin double bonds are also different.

It was found that the pore size of this kind of material can be fine-tuned via altering the kinds of anions and size of the organic ligands. The pore size of the anion-pillared hybrid porous materials are controlled within 3.0-6.0 Å, selective separation of C4 olefins (1,3-butadiene, 1-butene, 2-butene, and isobutene) with different molecular sizes can be achieved. The studies in the present invention show that the anions at various positions can form hydrogen bonds with different C4 olefin, then high C4 olefin separation efficiency can be achieved. Thus, C4 olefin mixtures can be efficiently separated by combining shape or molecular recognition and sieving-effect. Especially, the interpenetrated structures can adjust the geometry of the pores, thus endowing materials to match or recognize different C4 olefins with different configurations, and further enhance the adsorption selectivity and uptake capacity. For example, the present invention revealed that anion-pillared hybrid porous materials termed as SIFSIX-14-Cu-i has a high uptake capacity (2.4 mmol/g) for 1, 3-butadiene, and shows high 1, 3-butadiene/1-butene separation selectivity of 30. In addition, anion-pillared hybrid porous materials have high density of inorganic anion sites, then achieve high uptake capacity of C4 olefins. It shows that a kind of anion-pillared hybrid porous materials termed as SIFSIX-1-Cu has high uptake capacity for 1, 3-butadiene (7 mmol/g). The present invention shows that SIFSIX-2-Cu-i uptake 4 mmol/g 1, 3-butadiene, and shows high separation selectivity of 10 for 1, 3-butadiene and 1-butene. Therefore, this kind of anion-pillared hybrid porous materials has very high uptake capacity for C4 olefins, and exhibits highest separation selectivity compared with literature data. This kind of anion-pillared hybrid porous materials is one of the best adsorbents for the separation of C4 olefin mixtures.

DETAILED DESCRIPTION OF THE INVENTION

The present invention provides a method to separate C4 olefin mixtures using anion-pillared hybrid porous materials. The method comprises the contacting between the gas mixture with a hybrid porous material, wherein the anion-pillared hybrid porous material comprises a three-dimensional lattice of metal species (M), ligand groups (L) and inorganic anions (A). The metal ions coordinated with organic ligands forming two-dimensional layers, which then are pillared by inorganic anions to form three-dimensional frameworks. Suitably the hybrid porous material has the chemical formula: A-L-M.

The described "metal ion M" can comprise one or more of $Fe^{2+}$, $Co^{2+}$, $Ni^{2+}$, $Cu^{2+}$, and $Zn^{2+}$. Preferably, the metal ions are $Fe^{2+}$, $Co^{2+}$, $Cu^{2+}$.

The descried "inorganic anions A" can comprise one or more of $SiF_6^{2-}$, $TiF_6^{2-}$, $SnF_6^{2-}$, $ZrF_6^{2-}$, $GeF_6^{2-}$, or $NbF_6^{-}$.

The "inorganic anions A" can be divided into two classes as following:

The described $A_1F_6^{2-}$ can be specified as one or more of $SiF_6^{2-}$, $TiF_6^{2-}$, $SnF_6^{2-}$, $ZrF_6^{2-}$, $GeF_6^{2-}$.

The described $A_2F_6^{-}$ can be $NbF_6^{-}$.

The described "organic ligands L" disclosed herein comprises any of the three following kinds:

The first-class organic ligands L1 is selected from any of the following:

wherein $R_1$ is one of H, Cl, Br, I, OH, $NH_2$, and $CH_3$. $R_2$ is one of =O, $-NH_2$, and $-OH$.

The pore size of the hybrid porous materials constructed with this kind of organic ligand are within the range of 3-7 Å, and abundant anions lined by the pore walls.

Preferably, L1 can be one of 2,6-Diaminopurine, 2-Amino-6-chloropurine, and Guanine.

The second-class organic ligands L2 is selected from any of the following:

wherein, $R_3$, $R_4$, $R_5$, $R_6$, $R_7$, $R_8$, $R_9$, and $R_{10}$ can be individually one of H, F, Cl, Br, I, $CH_3$, $NH_2$, OH, and COOH;

The structure of the anion-pillared hybrid porous material prepared by the second type of organic ligand or ligand L2 and metal ions and inorganic anions is as follows:

The pore size of the anion-pillared hybrid porous materials constructed with organic ligand L2 are within the average range of 5-10 Å. The pore structure is one-dimensional channel, and every unit cell contains four anion pillars.

Preferably, L2 is selected as 4,4-bipyridine.

The third-class organic ligands L3 is selected from any of the following:

Wherein, $R_{11}$, $R_{12}$, $R_{13}$, $R_{14}$, $R_{15}$, $R_{16}$, $R_{17}$, and $R_{18}$ each can be independently selected from one of H, F, Cl, Br, I, $CH_3$, $NH_2$, OH, and COOH. $R_{19}$ is selected from any of following groups:

The third type of organic ligand L3 and the anion-pillared porous material prepared by the metal ion and the inorganic anion are a structure in which the channels are interpenetrated, as shown below:

The pore size of this framework is within the average range of 3-6 Å with anions intervened arrangement in the pore structures.

The preferred anion-pillared hybrid porous materials can be synthesized by the well-known ball-milling, interfacial diffusion method, solvothermal method and room stirring of reagents.

The present invention provides the method to efficiently separate C4 olefin mixtures, in which the mixture can contain two or more than two or more of 1-butene, iso-butene, 1,3-butadiene, trans-butene and cis-butene.

The present invention further describes the advantageous application fields of various materials.

A-L1-M in the anion-pillared hybrid porous material has a pore structure of 3 to 7 Å in size, and each channel unit contains a plurality of anions.

The organic ligand L1 in A-L1-M is 2-aminoadenine, and the anion-pillared hybrid porous material formed by 2-aminoadenine and metal ion M and inorganic anion AF6 has a pore diameter of 4~5 Å, and can selectively adsorb 1,3-butadiene, 1-butene, trans-2-butene, and almost no adsorption of isobutylene and cis-2-butene. Therefore, A-L1-M can achieve selective separation of the above C4 components.

Preferably, the organic ligand L1 in the anion-pillared hybrid porous material A-L1-M is 2-aminoadenine. The constructed anion-pillared hybrid porous materials formed by 2-aminoadenine, metal ion M and inorganic anion AF6 can selectively separate 1,3-butadiene, 1-butene, and iso-butene gas mixtures. The purity of the obtained iso-butene can be 99%, 70-99% purity for 1-butene, and 60-99% purity for 1,3-butadiene.

Preferably, the organic ligand L1 in the anion-pillared hybrid porous material A-L1-M is 2-aminoadenine. The constructed hybrid porous materials formed by 2-aminoadenine, metal ion M and inorganic anion AF6 can selectively separate trans-butene and cis-butene mixtures. The purity of the obtained trans-butene is higher than 99%, and the purity of the obtained cis-butene is more than 90%.

Preferably, the organic ligand L1 in the anion-pillared hybrid porous material A-L1-M is 2-aminoadenine. The constructed anion-pillared hybrid porous materials formed by 2-aminoadenine, metal ion M and inorganic anion AF6 can selectively separate 1-butene and 1,3-butadiene mixtures, through which the polymer-grade iso-butene and 1,3-butadiene can be obtained.

Most preferably, L1 is 2-aminoadenine, metal node is $Cu^{2+}$, and anion pillar is $TiF_6^{2-}$. The constructed anion-pillared hybrid porous materials A-L1-M can selectively separate 1-butene and 1,3-butadiene, in which the purity for 1-butene can reach higher than 99.999% and the purity for 1,3-butadiene can reach 90%.

The hybrid porous materials A-L2-M with pore size of 5-10 Å exhibit one-dimensional pore channels. There are four anions in each unit cell. This kind of material can realize the efficient separation of the mixture of 1-butene, iso-butene, and 1,3-butadiene. Trans-butene and cis-butene can also be separated. Preferably, A-L2-M is suitable for the separation of 1-butene and iso-butene mixtures.

Preferably, L2 is 4,4'-bipyridine. The obtained A-L2-M can selectively adsorb 1-butene, 1,3-butadiene, and trans-butene with low adsorption capacity for iso-butene and cis-butene, thus leading to the separation of C4 olefin mixtures. The obtained purity for iso-butene can be higher than 99%, 70-99% purity for 1-butene, and 60-99% purity for 1,3-butadiene.

Preferably, L2 is 4,4'-bipyridine. The obtained A-L2-M formed by 4,4'-bipyridine, metal ion M and inorganic anion AF6 can selectively separate cis-2-butene and trans-2-butene mixture. The obtained purity of cis-2-butene can be higher than 99% and the purity of and trans-2-butene can be higher than 90%.

Preferably, L2 is 4,4'-bipyridine. The obtained A-L2-M formed by 4,4'-bipyridine, metal ion M and inorganic anion AF6 can selectively separate 1-butene, 1,3-butadiene and iso-butene gas mixtures. The obtained purity of iso-butene can be higher than 99%, 70-99% purity for 1-butene, and 60-99% purity for 1,3-butadiene, respectively.

Preferably, L2 is 4,4'-bipyridine. The obtained A-L2-M formed by 4,4'-bipyridine, metal ion M and inorganic anion AF6 can selectively adsorb 1-butene and iso-butene, resulting in polymer-grade iso-butene and high purity 1-butene (>95%).

The hybrid porous materials A-L3-M with pore size of 3-6 Å exhibit interpenetrated structures. The inorganic anions are in staggered positions in the pore structures, which endow this material with excellent shape recognition ability, and selectively separate C4 olefins (1,3-butadiene, 1-butene, cis/trans 2-butene, isobutene).

Preferably, the formula of organic liner L3 in anion-pillared porous materials of $A-L_3-M$ is as bellowing:

wherein, $R_{19}$ can be any of the following groups:

Preferably, organic ligand $L_3$ can be any of 4,4'-dipyridylacetylene, 4,4'-azopyridine, 3-hydro-4,4'-bipyridylacetylene, 2-fluoro-4,4'-dipyridylacetylene.

Further selectively, organic ligand L3 in anion-pillared porous materials of A-$L_3$-M is 4,4'-dipyridylacetylene as following:

The interpenetrated structure of anion-pillared hybrid porous material formed by 4,4'-dipyridylacetylene in organic ligand L3 with metal ion M and inorganic anion AF6 exhibits the pore size of 3.0-5.5 Å, which can selectively adsorb 1-butene, 1,3-butadiene, and trans-2-butene, with little capture uptake for iso-butene and cis-2-butene. Therefore, C4 olefin mixtures can be separated.

Preferably, L3 is 4,4'-dipyridylacetylene. The obtained hybrid porous materials A-L3-M formed by 4,4'-dipyridylacetylene in organic ligand L3 with metal ion M and inorganic anion AF6 with interpenetrated structures can selectively separate 1-butene, 1,3-butadiene, and iso-butene mixtures. The purity of the obtained iso-butene can reach higher than 99%, 70-99% purity for 1-butene, and 60-99% purity for 1,3-butadiene, respectively.

Preferably, L3 is 4,4'-dipyridylacetylene. The obtained hybrid porous materials A-L3-M formed by 4,4'-dipyridylacetylene in organic ligand L3 with metal ion M and inorganic anion AF6 with interpenetrated structures can selectively separate 1-butene and 1,3-butadiene. The purity of the obtained 1-butene can be higher than 99% and 80-99% for 1,3-butadiene, respectively.

Preferably, L3 is 4,4'-dipyridylacetylene. The obtained hybrid porous materials A-L3-M formed by 4,4'-dipyridylacetylene in organic ligand L3 with metal ion M and inorganic anion AF6 with interpenetrated structures can selectively separate iso-butene and 1,3-butadiene. The obtained purity of iso-butene can be higher than 99% and 80-99% purity for 1,3-butadiene, respectively.

Preferably, L3 is 4,4'-dipyridylacetylene. The obtained hybrid porous materials A-L3-M formed by 4,4'-dipyridylacetylene in organic ligand L3 with metal ion M and inorganic anion AF6 with interpenetrated structures can selectively separate trans-2-butene and cis-2-butene. The obtained purity of cis-butene can be higher than 99% and 80-99% purity for trans-2-butene, respectively.

Further preferably, the hybrid porous material (A-L3-M) constructed by L3 4,4'-dipyridylacetylene, $Cu^{2+}$, and $SiF_6^{2+}$ can separate iso-butene (with purity more than 99.9%) from the mixtures of iso-butene, 1,3-butadiene, and 1-butene; it can also separate iso-butene and nitrogen mixture from 1,3-butadiene, 1-butene, iso-butene and nitrogen mixtures.

Further preferably, the hybrid porous material (A-L3-M) constructed by L3 4,4'-dipyridylacetylene, $Cu^{2+}$, and $NbF_6^-$ can separate iso-butene, cis-2-butene, and n-butane mixtures from the mixtures of 1,3-butadiene, 1-butene, iso-butene, trans-butene, cis-2-butene, n-butane, and propylene.

Further preferably, the organic ligand L3 is 4,4'-azopyridine, the formula is as bellowing:

Preferably, the pore size of the hybrid porous materials constructed by using 4,4'-azopyridine as organic ligand is in the range of 3-4.5 Å. The hybrid porous material formed by 4,4'-azopyridine in organic ligand L3 with metal ion M and inorganic anion AF6 with interpenetrated structures can selectively adsorb 1,3-butadiene and trans-2-butene, but have little uptake for 1-butene, iso-butene, and cis-2-butene. Thus, C4 olefins can be efficiently separated.

Most preferably, the organic ligand L3 is 4,4'-azopyridine. The hybrid porous material constructed by metal ion M, inorganic anion $AF_6$ with L3 exhibits interpenetrated structures. This material can selectively separate cis-2-butenes and trans-2-butenes with high purity cis-2-butene (higher than 99%) and trans-2-butene (higher than 96%) obtained.

Most preferably, the organic ligand L3 is 4,4'-azopyridine. The hybrid porous material constructed by metal ion M, inorganic anion $AF_6$ with L3 exhibits interpenetrated structures. This material can selectively separate cis-2-butenes and trans-2-butenes with high purity cis-2-butene (higher than 99%) and trans-2-butene (higher than 96%) obtained.

Most preferably, the organic ligand L3 is 4,4'-azopyridine. The hybrid porous material constructed by metal ion M, inorganic anion AF6 with L3 exhibits interpenetrated structures. This material can selectively separate iso-butene, 1,3-butadiene, and 1-butene mixtures, obtaining iso-butene and 1-butene mixtures with 1,3-butadiene less than 0.1%. The purity of 1,3-butadiene can be higher than 95%.

Most preferably, the organic ligand L3 is 4,4'-azopyridine. The hybrid porous material constructed by metal ion M, inorganic anion AF6 with L3 exhibits interpenetrated structures. This material can selectively separate iso-butene and 1,3-butadiene mixtures with high purity iso-butene (>99%) and 1,3-butadiene (>95%) obtained.

Most preferably, the organic ligand L3 is 4,4'-azopyridine. The hybrid porous material constructed by metal ion M, inorganic anion AF6 with L3 exhibits interpenetrated structures. This material can selectively separate iso-butene and 1,3-butadiene mixtures with high purity iso-butene (>99%) and 1,3-butadiene (>95%) obtained.

Most preferably, the interpenetrated hybrid porous material constructed by L3 4,4'-azopyridine, $Cu^{2+}$, and $SiF_6^{2-}$ can separate 1,3-butadiene from the mixtures of 1,3-butadiene, iso-butene, ethylene, and methane. The purity of 1,3-butadiene is higher than 96%; cis-2- and trans-2-butenes can also be separated with high purity cis-2-butene (>99.9%) obtained.

The method according to the present invention involves separating the specific C4 olefin mixtures with different compositions and concentrations. The concentrations of 1-butene, iso-butene, 1, 3-butadiene, cis-2-butene, and trans- 2-butene in the mixtures can ranged from 1% to 99%, and C4 olefin mixtures can be composed by two or more C4 olefins listed above. This kind of anion-pillared hybrid porous materials has good stability, and can be stable in the atmosphere of different amount of water, methane, nitrogen, carbon dioxide, hydrogen, butene, iso-butene, propy, acetylene, ethene, ethane, propane, and one or more components of C5.

According to the method of the present invention, the hybrid porous materials can be any of fixed bed adsorption separation, fluidized bed adsorption separation, moved bed adsorption separation, simulated moving bed adsorption separation, and membrane separation, in which the adsorption conditions can be temperature or pressure swing adsorption.

Preferably, the separation is conducted by fixed bed adsorption separation, comprising following steps:

(1) Passing C4 olefin mixtures through the column packed with hybrid porous materials under a specific temperature and pressures with a certain flow rate. The gas molecules that can strongly interact with hybrid porous materials are retained in the columns while other molecules with weak interactions with the materials or not adsorbed molecules breaking through the column. Thus, high purity specific C4 olefin that pre-breaking out the column can be obtained.

(2) After the specific C4 olefin broken out the column, the adsorption process is complete. The strongly adsorbed C4 component are desorbed by means of decompressing desorption, temperature increasing desorption, inert gas scavenging, or pure gas scavenging, then obtaining high purity strongly adsorbed C4 olefin.

In such embodiments, the activation and desorption temperature for the columns are between 10~200° C. Preferably, the temperature ranged from 35 to 120° C. The adsorbent described in the present invention is degassed by vacuum desorption, heating vacuum desorption, or heating while blow inert gas ($N_2$, He, Ar) with the pressure ranged from 0-1 atm.

Preferably, the adsorption of the gas mixture on the hybrid porous material is carried out at a temperature of from −20 to 60° C., preferably from 5 to 45° C.

Preferably, the contacting of the gas mixture with the hybrid porous material is carried out at a pressure of from 0.1 to 5 bar, preferably from 0.5 to 2 bar in the embodiments.

The shape of the above described adsorbents is particle, pellet, rod, or shaped spheres.

The highest purity of 1,3-butadiene, 1-butene, isobutene, cis-2-butene, and trans-2-butene obtained by separating C4 olefin mixture gas with ionic hybrid porous material is greater than 99%, and the highest purity is 99.999.%

In the present invention, the purity for polymer-grade is higher than 99.6%, high purity is higher than 90%.

In comparison with the prior art separation method, the outstanding advantages of the present invention are as follows:

(1) The present invention for the first time provides the separation method for C4 olefins using hybrid porous materials. The pore size and the positions of anions deposited in the pore structures can be fine-tuned, thus endowing the materials with excellent separation performance for C4 olefins by combing shape recognition and size-sieving.

(2) The hybrid porous materials can be easily synthesized and scale up under moderate conditions.

(3) Compared with conventional adsorbents, hybrid porous materials exhibit the advantages of fined-tuned pore size, pore volumes, and interaction between gas molecules with hybrid porous materials. Furthermore, this kind of materials exhibit high capacity and selectivity for C4 olefins.

(4) The high purity 1-butene, iso-butene, cis-2-butene, 1,3-butadiene, and trans-2-butene can be obtained. The highest purity can reach 99.999%.

(5) The provided separation method of the present invention has the merits of low energy consumption and fewer equipment investment compared with traditional solvent absorption and distillation methods. The hybrid porous materials can be regenerated and cyclically used with long lifetime, which is favorable for industrial applications.

Therefore, the separation method proposed in the present invention exhibit great potential in the separation and purification of C4 olefins, showing significant commercial implementation value and economic benefits

SPECIFIC EMBODIMENTS

Example 1

An acetonitrile and water (1:1 in volume) mixture solution (3 mL) was carefully dropped onto an aqueous solution (6 mL) containing 25.5 mg $Cu(BF_4)_2$~$H_2O$ and 19.7 mg $(NH_4)_2TiF_6$. Then a solution (4 mL, acetonitrile:water=1:1) containing 30.0 mg 2,6-Diaminopurine was dropped on the top of the solution. After 7 days, the obtained materials were filtrated and washed by methanol, then activated under vacuum conditions and 50° C. The resulted materials were MPM-2-TIFSIX.

Figure 1:
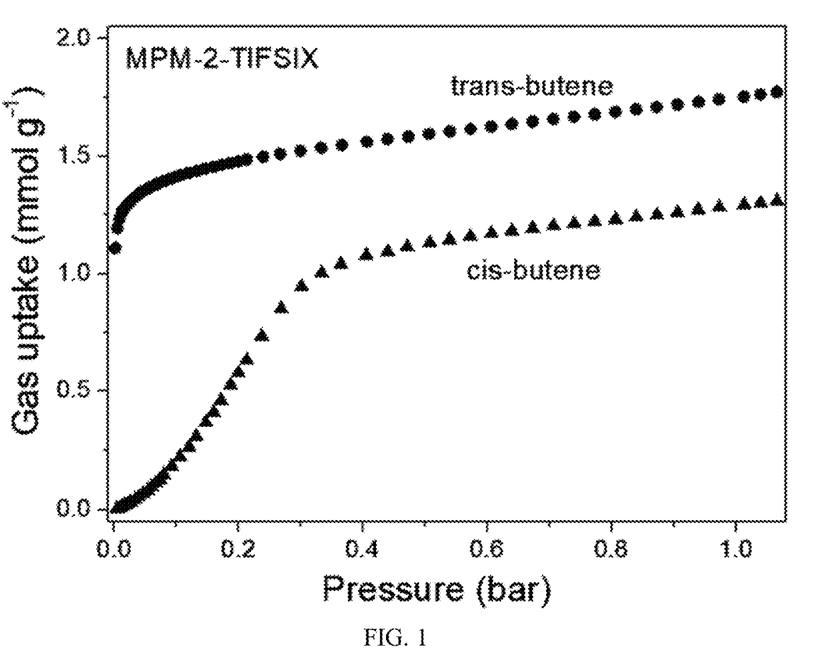
FIG. 1 shows the adsorption isotherms of cis-2-butene, trans-2-butene at 298 K on anion-pillared hybrid porous materials synthesized in example 1.

FIG. 1 presents the adsorption isotherms of cis-2-butenes and trans-2-butenes onto MPM-2-TIFSIX materials at 298 K.

Example 2

The obtained MPM-2-TIFSIX was packed into the column with length of 15 cm. Then the 1,3-butadiene and 1-butene (50:50 in volume) mixtures was flowed through the column with flow rate of 1.0 ml/min under 0.2 MPa. The high purity iso-butene (>99.999%) can be obtained. After 1,3-butadiene broke through the column, the separation process was done. The column was then degassed under vacuum conditions, leading to high purity 1,3-butadiene (>90%). The column then can be reused.

Example 3

The acetonitrile and water (1:1 in volume) mixture solution (3 mL) was carefully dropped onto the top of aqueous solution (6 mL) containing 27.7 mg $ZnSiF_6$. Then a solution (4 mL, acetonitrile:water=1:1 in volume) containing 50.0 mg 2-Amino-6-chloropurine was dropped onto the solution. After 4 days, the obtained materials were filtrated and washed by methanol, then activated under vacuum conditions and 70° C. The resulted materials were MPM-3-SIFSIX.

Example 4

An acetonitrile and water (1:1 in volume) mixture solution (3 mL) was carefully dropped onto the aqueous solution (6 mL) containing 32.8 mg $Cu(NO_3)_2 \cdot 3H_2O$ and 17.7 mg $(NH_4)_2SiF_6$. Then a solution (4 mL, acetonitrile:water=1:1 in volume) containing 30.0 mg adenine was dropped on the top of the solution. After 5 days, the obtained materials were filtrated and washed by acetonitrile, then activated under vacuum conditions at room temperature for 2 days. The resulted materials were MPM-4-TIFSIX.

Example 5

The obtained MPM-4-TIFSIX was packed into the column with length of 5 cm. Then trans-2-butene and cis-2-butene (50:50 in volume) mixtures was flowed through the column with flow rate of 1.0 ml/min under 0.1 MPa. The high purity cis-butene (>99.999%) can be obtained. When trans-2-butene broke through the column, the separation process was done. The column was then degassed under vacuum conditions, leading to high purity trans-2-butene (>95%). The column then can be reused.

Example 6

1,3-butadiene and iso-butene (95:5 in volume) mixtures was flowed through the column with flow rate of 1.0 mL/min under 0.2 MPa. The high purity iso-butene (>99.99%) can be obtained. When 1,3-butadiene broke out, the separation process was done. The column was then degassed under vacuum conditions at 60° C., leading to high purity 1,3-butadiene (>90%). The column then can be reused.

Example 7

125.0 mg $Fe(BF_4)_2 \cdot H_2O$ and 90.0 mg $(NH_4)_2SiF_6$ were dissolved into 10 mL water in a bottle, then mixed with methanol solution containing 190.0 mg 2-fluoro-4,4'-dipyridylacetylene under stirring. Then the capped bottle was heated at 85° C. for 12 hours. The resulted products were then filtered and washed by methanol, then activated under vacuum conditions for 24 hours. The resulted materials were SIFSIX-2F-Fe-i.

Example 8

125.0 mg $Co(BF_4)_2 \cdot H_2O$ and 100.0 mg $(NH_4)_2GeF_6$ were dissolved into 10 mL water in a bottle, then mixed with methanol solution containing 205.0 mg 3-fluoro-4,4'-dipyridylacetylene under stirring. Then the capped bottle was heated at 60° C. for 12 hours. The resulted products were then filtered and washed by methanol, then activated under vacuum conditions for 24 hours. The resulted materials were GeFSIX-2-OH-Co-i.

Example 9

The activated GeFSIX-2-OH-Co-i of Example 8 was packed into the column (inner diameter 4.6 mm, length 50 mm). iso-butene and 1-butene (70:30 in volume) was introduced into the column with flow rate of 1.5 mL/min under 0.1 MPa and 25° C. The polymer-grade of iso-butene (>99.999%) can be obtained. When 1-butene broke through the column, the separation process was over. The column was then purged by He for 15 hours. The column then can be reused.

Example 10

An aqueous solution dissolved 270.0 mg $Co(BF_4)_2 \cdot xH_2O$ and 200.0 mg $(NH_4)_2SiF_6$ dropped into the glycol solution containing 4,4'-bipyridine under stirring. Then the resulted solution was heated at 60° C. for 3 hours. The resulted products were filtered and washed by methanol, then immersed into methanol for 3 days. After filtered, SIFSIX-1-Cu was obtained.

The activated SIFSIX-1-Cu was loaded into the column (inner diameter 4.6 mm, length 250 mm). iso-butene and 1-butene (50:50 in volume) was introduced into the column with flow rate of 1.0 mL/min under 0.2 MPa at room temperature. The polymer-grade of iso-butene (>99.9%) can be obtained. When 1-butene broke through the column, the separation process was over. The column was then degassed under vacuum condition at 40° C., leading to the high purity 1-butene (>95%). The column then can be reused.

Example 11

1,3-butadiene and ethane (60:40 in volume) mixture was introduced into the column of SIFSIX-1-Cu, the high purity ethane (99.99%) can be obtained. When 1,3-butadiene broke through the column, the adsorption was stopped. The column with adsorbed 1,3-butadiene was desorbed under vacuum conditions for 24 hours, and then could be reused.

Example 12

125.0 mg $Cu(BF_4)_2 \cdot H_2O$ and 90.0 mg $(NH_4)_2SiF_6$ were dissolved into 10 mL water in a bottle, then mixed with methanol solution containing 182.0 mg 4,4'-dipyridylacetylene under stirring, and then stirring for 24 hours at room temperature. The resulted products were then filtered and washed by methanol, then activated under vacuum 50° C. for 24 hours. The resulted materials were SIFSIX-2-Cu-i.

Figure 2:
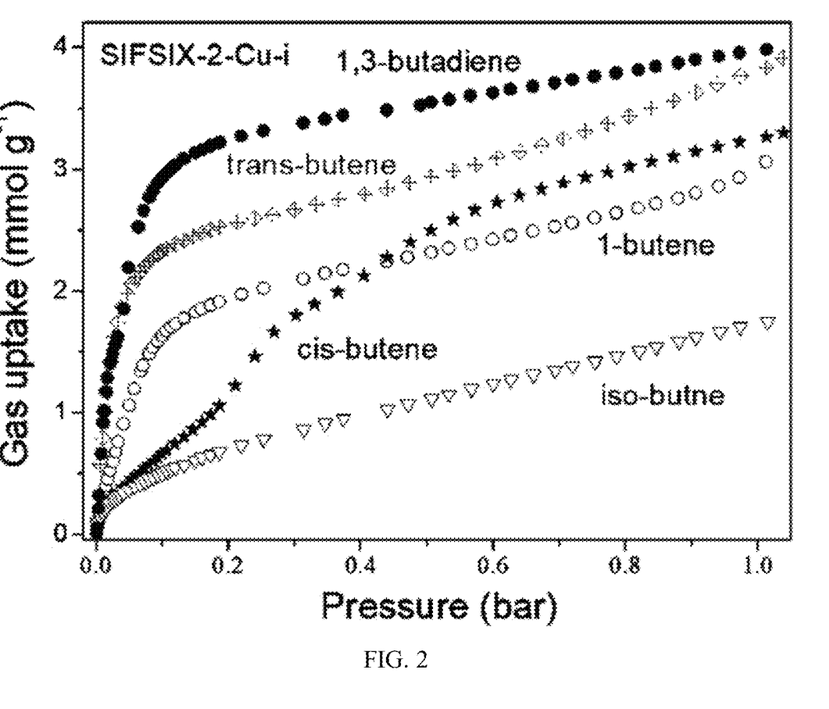
FIG. 2 shows the adsorption isotherms of 1, 3-dutadiene, 1-butene, iso-butene, cis-2-butene, trans-2-butene at 298 K on anion-pillared hybrid porous materials synthesized in example 12.

FIG. 2 presents the adsorption isotherms of 1,3-butadiene, 1-butene, iso-butene, cis-butene, and trans-butene on SIFSIX-2-Cu-i at 25° C.

Example 13

Figure 3:
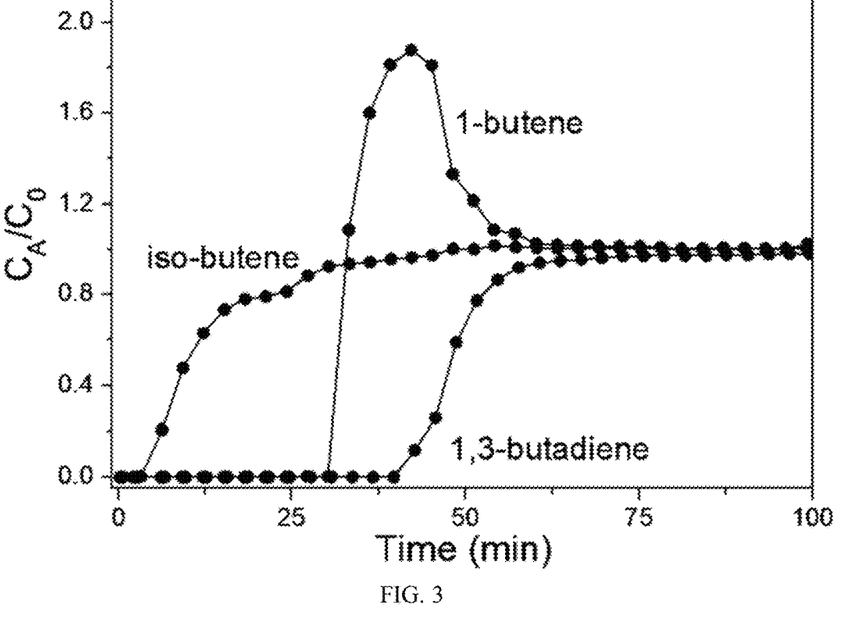
FIG. 3 shows the breakthrough curves of example 13.

The activated SIFSIX-2-Cu-i was loaded into the column (inner diameter 4.6 mm, length 100 mm). The iso-butene, 1-butene, 1,3-butadiene and He (30:15:50:5 om volume) was introduced into the column with flow rate of 1.5 mL/min under 0.1 MPa at 30° C. The polymer-grade of iso-butene (>99.999%) can be obtained. When 1-butene broke through the column, the adsorption was stopped. The column was purged with He for 15 hours, the column could be reused. FIG. 3 shows the breakthrough curves of iso-butene, 1-butene, 1,3-butadien and He (30:15:50:5) on SIFSIX-2-Cu-i.

Example 14

Figure 4:
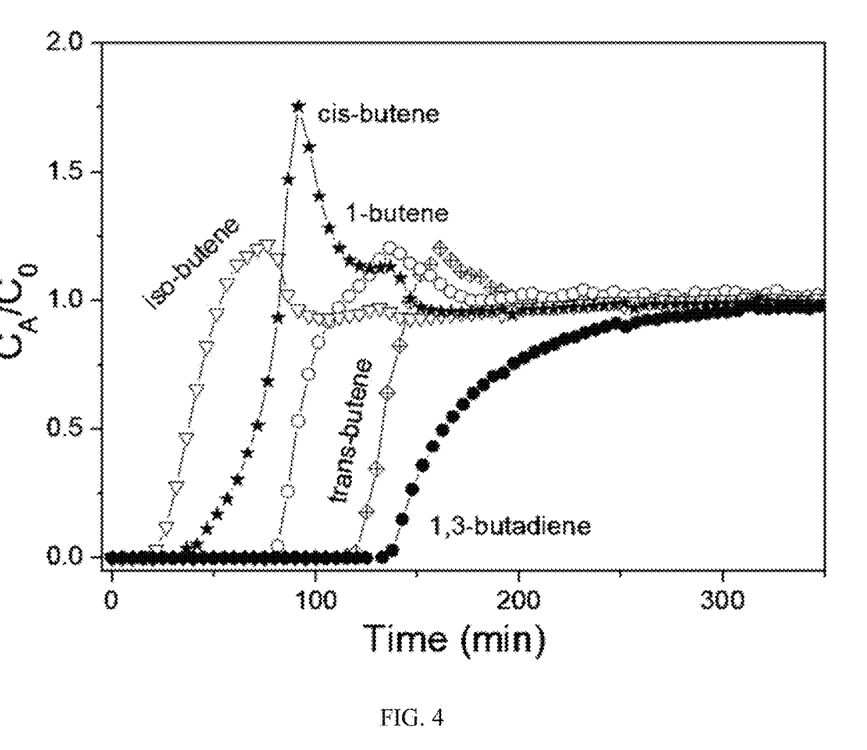
FIG. 4 shows the breakthrough curves of example 14.

The mixture comprising of iso-butene, 1-butene, 1,3-butadiene, cis-2-butene and trans-2-butene (20:20:20:20:20 in volume) was introduced into the column of SIFSIX-2-Cu-i. When 1,3-butadiene broke through the column, the adsorption was stopped. The column was then purged with He for 12 h, the column could be reused. FIG. 4 show the breakthrough curves of iso-butene, 1-butene, 1,3-butadiene, cis-butene and trans-butene (20:20:20:20:20) mixtures on SIFSIX-2-Cu-i, indicating the separation ability of SIFSIX-2-Cu-i for C4 olefins.

Example 15

The mixture comprising of iso-butene and 1,3-butadiene (50:50 in volume) was introduced into the column of SIFSIX-2-Cu-i with flow rate of 0.5 mL/min at 40° C. When iso-butene broke out the column with high purity (>99.99%). When 1,3-butadiene broke through the column, the adsorption was stopped. The column was then degassed under vacuum conditions, resulting in 1,3-butadiene with purity higher than 90%, and then the column could be reused.

Example 16

Figure 5:
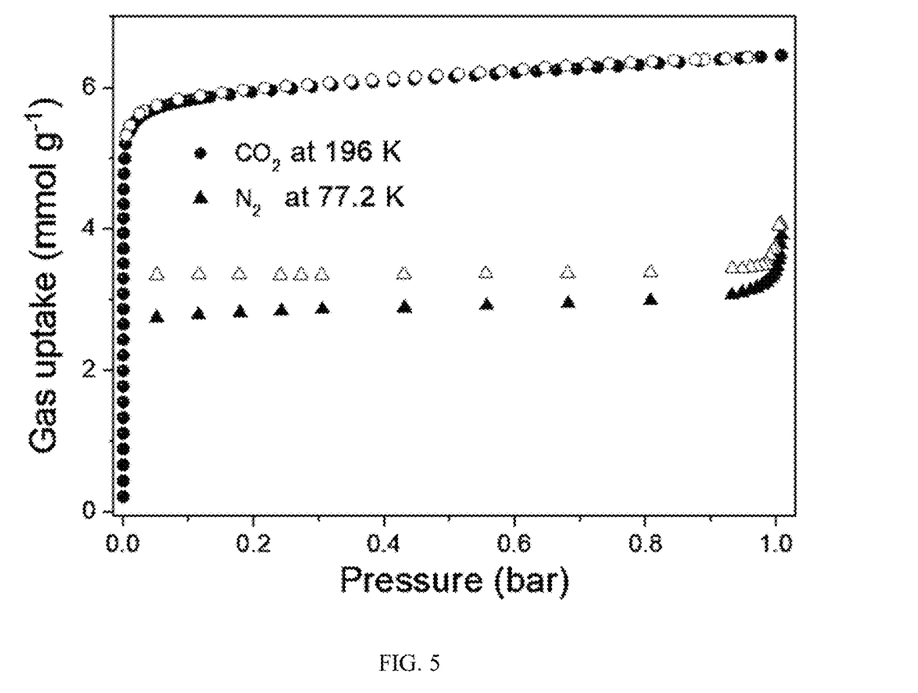
FIG. 5 shows the adsorption isotherms of $N_2$ (77 K) and $CO_2$ (196 K) on anion-pillared hybrid porous materials synthesized in example 16.
Figure 6:
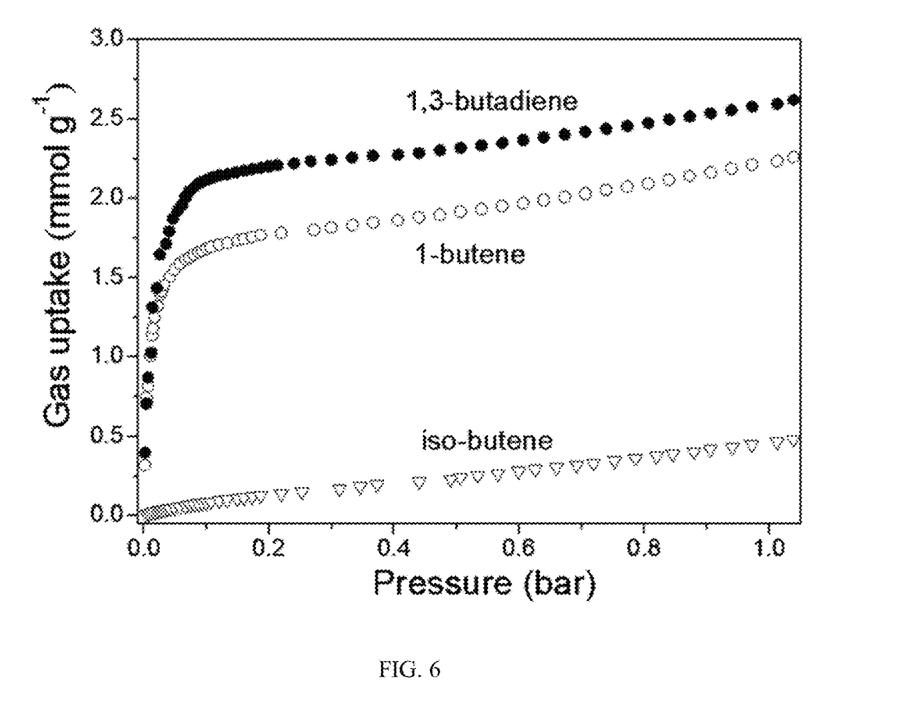
FIG. 6 shows the adsorption isotherms of 1, 3-dutadiene, 1-butene, iso-butene, cis-2-butene, trans-2-butene at 298 K on anion-pillared hybrid porous materials synthesized in example 16.

A methanol solution (10 mL) containing 182.0 mg 4,4'-dipyridylacetylene was carefully dropped on the top of glycol and methanol solution (20 mL, 1:1 in volume) containing 125.0 mg $Cu(BF_4)_2.H_2O$ and 122.0 mg $NH_4NbF_6$. After 3 days, the resulted products were then filtered and washed with methanol, and then activated by purging N2 flow at 45° C. for 24 hours. The resulted materials were NbFSIX-2-Cu-i. FIG. 5 shows the adsorption isotherms of N2 (77.2 K) and CO2 (196 K) on NbFSIX-2-Cu-i; FIG. 6 shows the adsorption isotherms of 1,3-butadiene, 1-butene, and iso-butene on NbFSIX-2-Cu-i at 25° C. (298K).

Example 17

Figure 7:
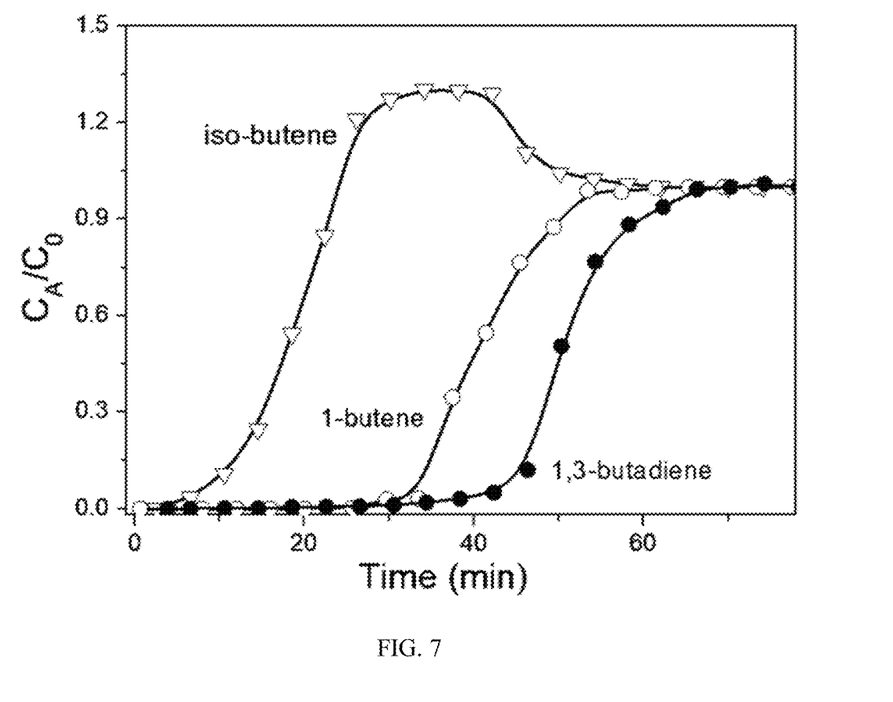
FIG. 7 shows the breakthrough curves of example 17.

The activated NbFSIX-2-Cu-i obtained in Example 16 was packed into the 5 cm column. The 1,3-butadiene, 1-butene, iso-2-butene, and He (50:15:25:10 in volume) was introduced into the column with flow rate of 2.0 mL/min under 0.1 MPa at 15° C. The iso-butene and 1-butene mixtures broke out the column firstly, when the second component broke through, the adsorption was stopped. The column was purged with $N_2$ for 15 hours at 50° C., the column could be reused. FIG. 7 shows the breakthrough curves of 1,3-butadiene:1-butene:iso-butene:He (50:15:25:10) mixtures on NbFSIX-2-Cu-i.

Example 18

Figure 8:
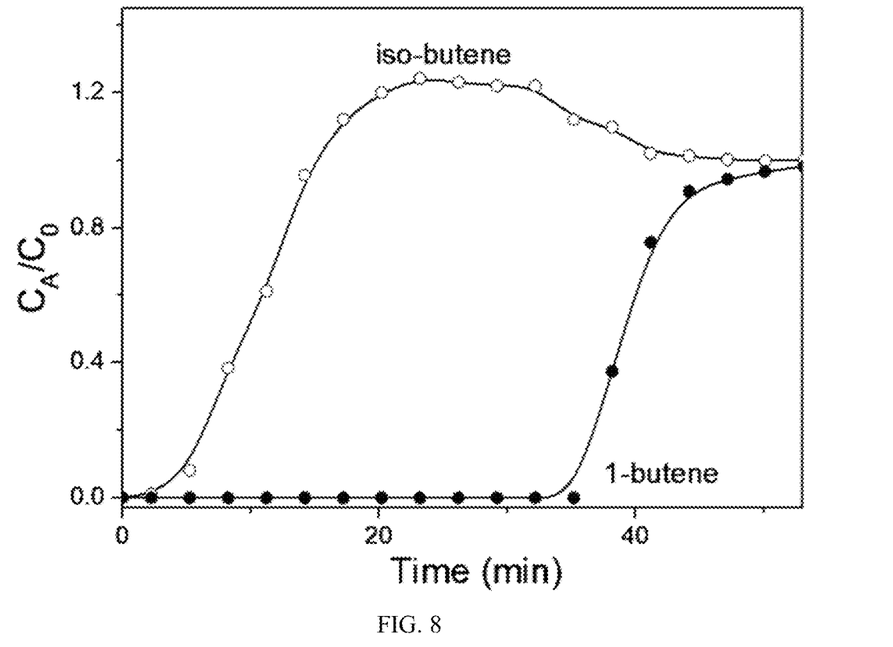
FIG. 8 shows the breakthrough curves of example 18.

The 1-butene and iso-butene (50:50 in volume) was introduced into the column of Example 17 with a flow rate of 0.5 mL/min under 0.2 MPa at 10° C. The iso-butene (>99.99%) broke out the column. When 1-butene breaks out the column, the adsorption was stopped. The column was purged with He for 12 hours at room temperature, the column could be reused. FIG. 8 presents the breakthrough curves of 1-butene:iso-butene (50:50) mixtures on NbFSIX-2-Cu-i.

Example 19

The 1,3-butadiene:1-butene:iso-butene:iso-butane (50:15:35:5 in volume) was introduced into the column of NbFSIX-2-Cu-i as in Example 17 with flow rate of 1.0 mL/min under 1 MPa at 10° C. The iso-butene and iso-butane mixtures can be firstly obtained. When 1-butene broke out the column, the adsorption was stopped. The column was purged with He for 12 hours at room temperature, the column could be reused.

Example 20

The 1-butene:cis-2-butene (50:50 in volume) mixture was introduced into the column of NbFSIX-2-Cu-i as in Example 17 with flow rate of 0.5 mL/min under 0.2 MPa at 30° C. The cis-2-butene with purity higher than 99.99% can be firstly obtained. When 1-butene broke out the column, the adsorption was stopped. The column was degassed under vacuum conditions, the column could be reused.

Example 21

A methanol solution (10 mL) containing 196.0 mg 4,4'-Dipyridyl disulphide was mixed with the glycol and methanol solution (15 mL, 1:1 in volume) containing 125.0 mg $Co(BF_4)_2.H_2O$ and 90.0 mg $(NH_4)2NSiF_6$. The resulted solution was heated to 60° C. for 24 hours, the products were then filtered and washed with methanol, and then activated under vacuum conditions at 40° C. The resulted materials were SIFSIX-S-Co-i.

Example 22

The 1,3-butadiene:cis-2-butene:methane:propane (2:1:1:1 in volume) mixture was introduced into the column (inner diameter 4.6 mm, length 100 mm) packed with SIFSIX-S-Co-i with flow rate of 1.0 mL/min. When 1,3-butadiene broke out the column, the adsorption was stopped. The column was degassed under vacuum condition, which resulted in 1,3-butadiene with high purity (>90%), then the column could be reused.

Example 23

The cis-2-butene:trans-2-butene (50:50 in volume) mixture was introduced into the SIFSIX-S-Co-i column with flow rate of 1.0 mL/min at 10° C. High purity cis-2-butene (99.99%) can be obtained, when trans-2-butene broke out the column, the adsorption was stopped. The column was purged with He for 12 hours, then the column could be reused.

Example 24

A methanol solution (25 mL) of 138.0 mg $CuSiF_6$ was mixed with another methanol solution containing 98.0 mg 4,4'-azopyridine, the mixture was then stirred for 24 hours at room temperature. The resulted products were then filtered and washed with methanol, and then activated by under vacuum condition at 40° C. for 24 hours. The resulted materials were SIFSIX-14-Cu-i.

Figure 9:
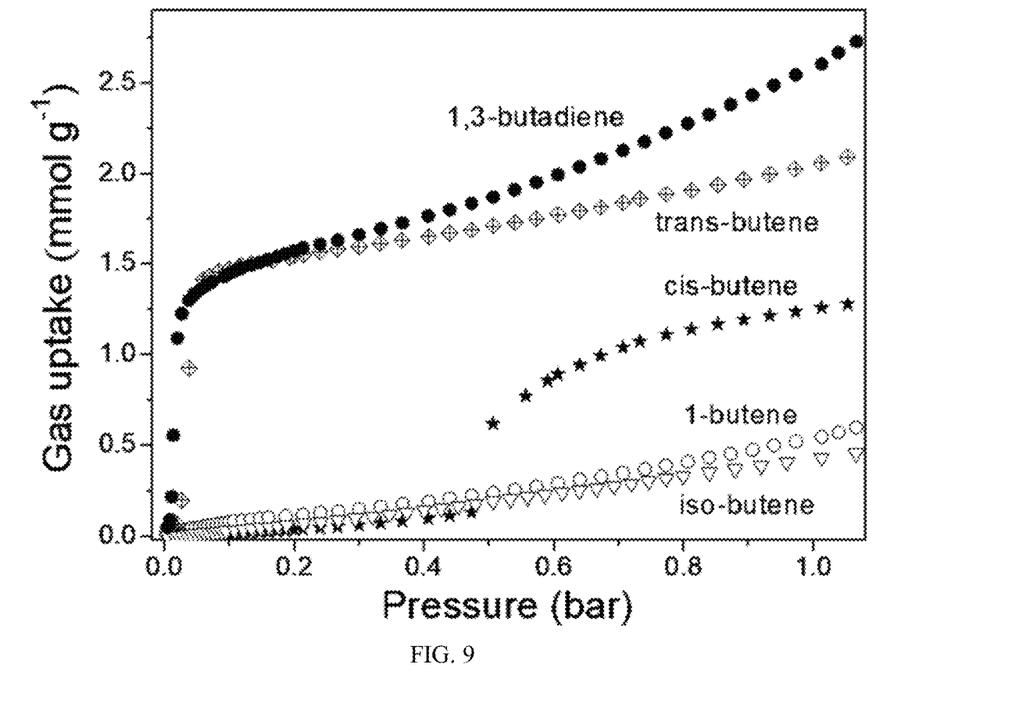
FIG. 9 shows the adsorption isotherms of 1, 3-dutadiene, 1-butene, iso-butene, cis-2-butene, trans-2-butene at 298 K on anion-pillared hybrid porous materials synthesized in example 24.

FIG. 9 exhibits the adsorption isotherms of 1,3-butadiene, 1-butene, iso-butene, trans-2-butene and cis-2-butene on SIFSIX-14-Cu-I under 298K.

Example 25

The SIFSIX-14-Cu-i material was packed into the column (inner diameter 4.6 mm, length 150 mm), and then the mixture of 1,3-butadiene:iso-butene:ethylene:methane (50:50:5:5 in volume) was introduced into the column with flow rate of 2.5 mL/min. The outflow gas is iso-butene, ethylene and methane mixtures. when 1,3-butadiene broke through the column, the adsorption was stopped. The column was purged with 1,3-butadiene, and then degassed under vacuum condition, leading to high purity 1,3-butadiene (>99%), the column could be reused.

Example 26

The mixture of trans-2- and cis-2-butenes (50:50 in volume, 0.1 MPa) was introduced into the SIFSIX-14-Cu-i column with flow rate of 1.0 mL/min at 25° C. High purity cis-butene (higher than 99.99%) firstly broke through the column, when trans-2-butene broke out, the adsorption was stopped. The column was purged with He to desorb trans-2-butene, then the column could be reused.

Example 27

Figure 10:
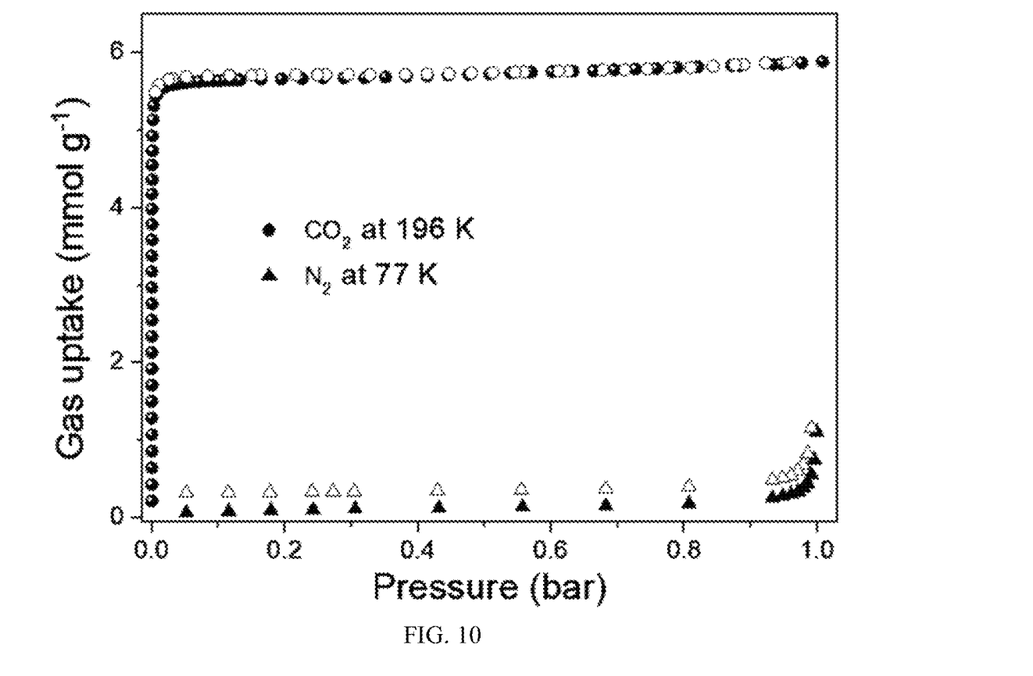
FIG. 10 shows the adsorption isotherms of $N_2$ (77 K) and $CO_2$ (196 K) on anion-pillared hybrid porous materials synthesized in example 27.
Figure 11:
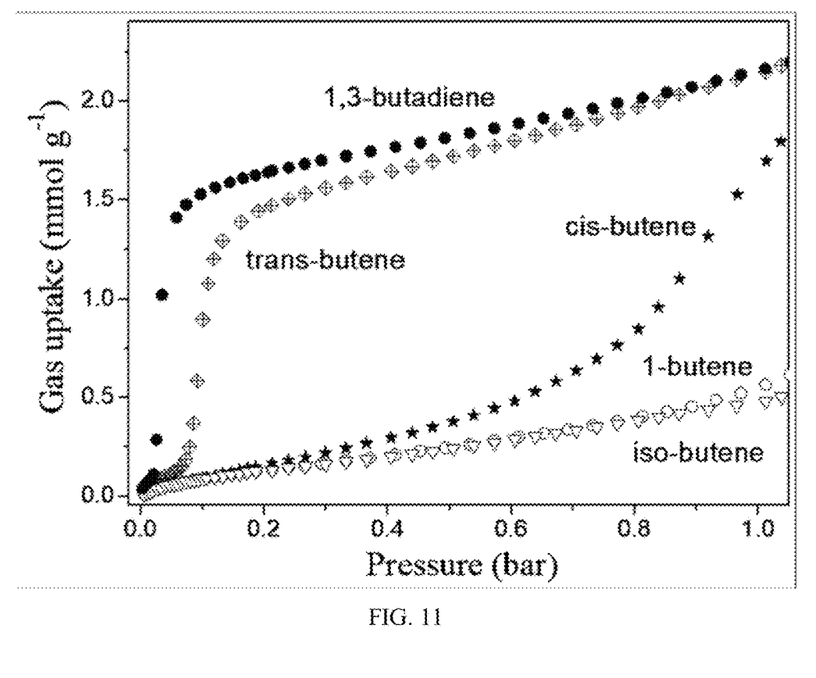
FIG. 11 shows the adsorption isotherms of 1, 3-dutadiene, 1-butene, iso-butene, cis-2-butene, trans-2-butene at 298 K on anion-pillared hybrid porous materials synthesized in example 27.
Figure 12:
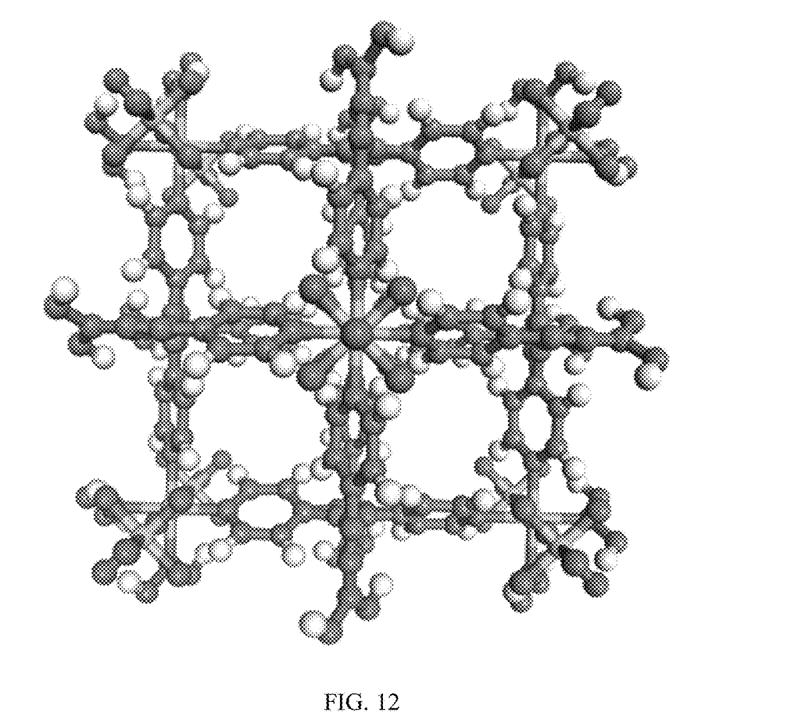
FIG. 12 shows the crystal structure of anion-pillared hybrid porous materials synthesized in example 27.

A methanol solution (20 mL) containing 244.0 mg $Cu(BF_4)_2.3H_2O$ and 272.0 mg $(NH_4)_2GeF_6$ was mixed with 360.0 mg 4,4'-azopyridine in methanol solution (20 mL). The mixture was stirred at room temperature for 12 hours, then filtered and washed methanol. The resulted products were then purged with N2 for 24 hours at 45° C., leading to GEFSIX-14-Cu-i. FIG. 10 presents the $N_2$ (77 K) and $CO_2$ (196 K) adsorption isotherms on GEFSIX-14-Cu-i; FIG. 11 presents the adsorption isotherms of 1,3-butadiene, 1-butene, iso-butene, cis-butene and trans-butene on GEFSIX-14-Cu-i at 298 K. FIG. 12 illustrates the crystal structures of GEFSIX-14-Cu-i.

Example 28

Figure 13:
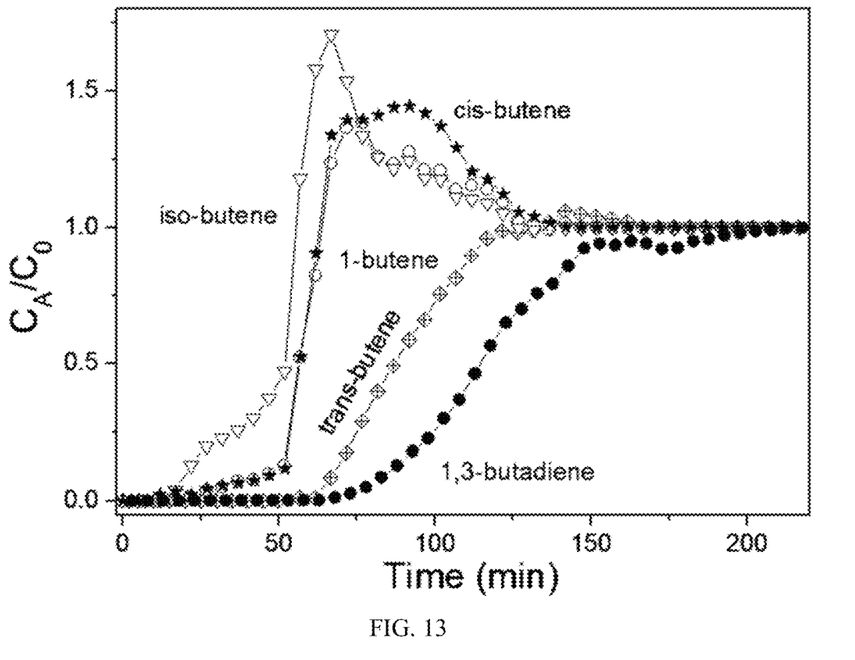
FIG. 13. shows the breakthrough curves of example 28.

The obtained GEFSIX-14-Cu-i was packed into the column of 10 cm (inner diameter 4.6 mm, length 150 mm), into which then introduced the mixtures of 1,3-butadiene:iso-butene:1-butene:trans-2-butene:cis-2-butene (20:20:20:20:20) with flow rate of 1.0 mL/min at 20° C. When 1,3-butadiene broke out the column, the adsorption was stopped. The column was purged with 1,3-butadiene to remove the adsorbed trans-butene, then 1,3-butadiene was desorbed from the column under vacuum with high purity 1,3-butadiene (>99%) obtained, then the column could be reused. FIG. 13 shows the corresponding breakthrough curves.

Example 29

The mixtures of 1,3-butadiene, iso-butene, and iso-butane (80:15:5 in volume) was introduced into the GEFSIX-14-Cu-i column of Example 28 with flow rate of 1.0 mL/min at 35° C. The iso-butene and iso-butane mixture with 1,3-butadiene less than 10 ppm was obtained. When 1,3-butadiene broke through the column, the adsorption process was stopped. Then 1,3-butadiene was used to remove the adsorbed iso-butene and iso-butane onto GEFSIX-14-Cu-i column, after that, high purity 1,3-butadiene (more than 97%) could be obtained by degassing the column under vacuum, and the column could be reused.

Example 30

The mixtures of 1,3-butadiene, 1-butene, iso-butene, cis-2-butene, trans-2-butene, and iso-butane (50:10:25:5:5 in volume) was introduced into the GEFSIX-14-Cu-i column of Example 28 with flow rate of 2.0 ml/min at 20° C. Then the NbFSIX-2-Cu-i column under 10° C. was connected back with GEFSIX-14-Cu-i column. When 1-butene broke through the column, the adsorption was stopped. GEFSIX-14-Cu-i column was then purged with 1,3-butadiene to remove trans-2-butene, then this column was degassed under vacuum, resulting high purity 1,3-butadien (higher than 97%), then the column could be reused. The NbFSIX-2-Cu-i column was degassed under vacuum, resulting in high purity 1-butene (95%), the column could be reused.

Example 31

A methanol solution (10 mL) containing 185.0 mg 4,4'-azopyridine was carefully dropped onto 20 mL glycol and methanol solution (1:1 in volume) containing 125.0 mg $CuCl_2.H_2O$ and 117.0 mg $NH_4NbF_6$. After one week, the obtained products were filtered and washed with methanol, the resulted samples were activated under vacuum for 24 hours, leading to NbFSIX-14-Cu-i.

Example 32

The obtained NbFSIX-14-Cu-i was packed into the column of 10 cm, then the mixture of 1-butene:iso-butene:propane (40:40:20 in volume) with flow rate of 1.0 mL/min. The mixture of iso-butene and propane firstly broke out the column, when 1-butene broke through the column, the adsorption was stopped. Then high purity 1-butene (97%) was desorbed from the column under vacuum, then the column could be reused.

Furthermore, the foregoing descriptions of the embodiments according to the present invention are provided for illustration only, not for the purpose of limiting the invention as defined by the appended claims and their equivalents. Although only the selected embodiments have been chosen to illustrate the present invention, the all involved change or modification without departing from the scope of the invention as defined in the appended claims are covered in this invention.

The invention claimed is:

1. A method of separating C4 olefins by using anion-pillared hybrid porous materials as a separation material, comprising a step of contacting the separation material with C4 olefins to achieve separation, wherein the C4 olefins are any two or more of 1-butene, iso-butene, 1,3-butadiene, cis-2-butene, and trans-2-butene;

the hybrid porous materials are constructed by metal ions, inorganic anions, and organic ligands, in which the metal ions, the inorganic anions, and the organic ligands link together through coordination bonds forming a three-dimensional framework with formula of A-L-M;

wherein the metal ions, M, are one or more of $Fe^{2+}$, $Co^{2+}$, $Ni^{2+}$, $Cu^{2+}$;

wherein the inorganic anions, A, are one or more of $SiF_6^{2-}$, $TiF_6^{2-}$, $SnF_6^{2-}$, $GeF_6^{2-}$, or $NbF_6^{-}$, and $NbOF_5^{2-}$;

wherein the organic ligand L is selected from the group consisting of 2,6-Diaminopurine, 2-Amino-6-chloropurine, and Guanine.

2. A method of separating C4 olefins by using anion-pillared hybrid porous materials as a separation material, comprising a step of contacting the separation material with C4 olefins to achieve separation, wherein the C4 olefins are any two or more of 1-butene, iso-butene, 1,3-butadiene, cis-2-butene, and trans-2-butene;

the hybrid porous materials are constructed by metal ions, inorganic anions, and organic ligands, in which the metal ions, the inorganic anions, and the organic ligands link together through coordination bonds forming a three-dimensional framework with formula of A-L-M;

wherein the metal ions, M, are one or more of $Fe^{2+}$, $Co^{2+}$, $Ni^{2+}$, $Cu^{2+}$;

wherein the inorganic anions, A, are one or more of $SiF_6^{2-}$, $TiF_6^{2-}$, $SnF_6^{2-}$, $GeF_6^{2-}$, or $NbF_6^{-}$, and $NbOF_5^{2-}$;

wherein the organic ligand L is 2,6-Diaminopurine;

wherein the resulted hybrid porous materials A-L-M can separate 1-butene and 1,3-butadiene mixtures with polymer-grade of iso-butene and high purity 1,3-butadiene obtained; or can separate the mixtures of 1,3-butadiene, 1-butene, trans-2-butene, iso-butene and cis-2-butene; or can separate 1,3-butadiene and iso-butene mixtures with polymer-grade of iso-butene obtained; or can separate 1-butene and iso-butene mixtures with polymer-grade of iso-butene obtained; or can separate trans-2-butene and cis-2-butene mixtures with polymer-grade of cis-2-butene and high purity trans-butene obtained.

3. The method of separating C4 olefins according to claim 1, wherein the contacting between the gas mixture with a hybrid porous material is selected from the group consisting of fixed bed adsorption separation, fluidized bed adsorption separation, moving bed adsorption separation, simulated moving bed adsorption separation, and membrane separation.

4. The method of separating C4 olefins according to claim 1, wherein the contacting is in fixed bed adsorption, and the steps are as following:

(1) C4 olefin mixtures passing through a column packed with the anion-pillared hybrid porous materials under a pre-determined temperature and pressure with a pre-determined flow rate, wherein C4 olefins which interact with hybrid porous materials are retained in the column while other C4 compounds are not retained in the column;

(2) after breakthrough of the retained C4 olefins, stopping the adsorption process in step (1), desorbing the C4 olefins retained in the column by means of decompressing desorption, temperature increasing desorption, inert gas scavenging, or pure gas scavenging, then obtaining the C4 olefins.

* * * * *